(12) United States Patent
Costa et al.

(10) Patent No.: US 6,839,661 B2
(45) Date of Patent: Jan. 4, 2005

(54) SYSTEM FOR NORMALIZING SPECTRA

(75) Inventors: Peter J. Costa, Hudson, MA (US); Kwong Hui, Woburn, MA (US); Robert J. Nordstrom, Hanover, MA (US)

(73) Assignee: MediSpectra, Inc., Lexington, MA (US)

( * ) Notice: Subject to any disclaimer, the term of this patent is extended or adjusted under 35 U.S.C. 154(b) by 426 days.

(21) Appl. No.: 09/738,612

(22) Filed: Dec. 15, 2000

(65) Prior Publication Data

US 2002/0107668 A1 Aug. 8, 2002

(51) Int. Cl.[7] ............................................. G06F 15/00
(52) U.S. Cl. .................................................... 702/189
(58) Field of Search ............................ 702/69, 75–77, 702/189, 199; 600/473, 476, 478

(56) References Cited

U.S. PATENT DOCUMENTS

| | | | |
|---|---|---|---|
| 3,013,467 A | 12/1961 | Minsky | 88/14 |
| 3,632,865 A | 1/1972 | Haskell et al. | 178/6 |
| 3,809,072 A | 5/1974 | Ersek et al. | 128/23 |
| 3,890,462 A | 6/1975 | Limb et al. | 178/6.8 |
| 3,963,019 A | 6/1976 | Quandt et al. | 128/2 |
| D242,393 S | 11/1976 | Bauman | |
| D242,396 S | 11/1976 | Bauman | |
| D242,397 S | 11/1976 | Bauman | |
| D242,398 S | 11/1976 | Bauman | |
| 4,017,192 A | 4/1977 | Rosenthal et al. | 356/201 |
| 4,071,020 A | 1/1978 | Puglise | 128/2 |
| 4,198,571 A | 4/1980 | Sheppard | 250/571 |
| 4,218,703 A | 8/1980 | Netravali et al. | 358/136 |
| 4,254,421 A | 3/1981 | Kreutel, Jr. | 343/754 |
| 4,273,110 A | 6/1981 | Groux | 128/6 |
| 4,357,075 A | 11/1982 | Hunter | 350/294 |

(List continued on next page.)

FOREIGN PATENT DOCUMENTS

| | | |
|---|---|---|
| EP | 0 135 134 | 3/1985 |
| EP | 0 280 418 | 8/1988 |
| EP | 0 335 725 | 10/1989 |

(List continued on next page.)

OTHER PUBLICATIONS

Agrawal et al. (1999), "Fluorescence Spectroscopy of the Cervix: Influence of Acetic Acid, Cervical Mucus, and Vaginal Medications," *Lasers in Surgery and Medicine*, 25:237–249.

Althof et al. (1997), "A rapid and automatic image registration algorithm with subpixel accuracy," *IEEE Transactions on Medical Imaging*, 16(3):308–316.

Aström et al. (1999), "Motion estimation in image sequences using the deformation of apparent contours," *IEEE Transactions on Pattern Analysis and Machine Intelligence*, 21(2):114–127.

(List continued on next page.)

*Primary Examiner*—Michael Nghiem
(74) *Attorney, Agent, or Firm*—Testa, Hurwitz & Thibeault, LLP (57) ABSTRACT

A method and system for normalizing optical spectra using a non-uniform segment normalization. A spectrum is obtained and is represented as a function of wavelength as an amplitude at each of a plurality of wavelengths. At least one segment of the spectrum is selected, each selected segment being bounded by an upper wavelength and a lower wavelength. A normalization factor is computed as the sum of the areas for each of the selected segments. The spectrum is normalized by dividing at least one amplitude of the spectrum by the normalization factor. Segments can be selected with different wavelength ranges, that is, segments can be non-uniform. Test specimens can be categorized based on an analysis of normalized spectra. In particular, the specimen to be tested can be human cervical tissue, and the state of health of the tissue can be determined.

19 Claims, 5 Drawing Sheets

U.S. PATENT DOCUMENTS

| | | | |
|---|---|---|---|
| 4,397,557 A | 8/1983 | Herwig et al. | 356/342 |
| 4,549,229 A | 10/1985 | Nakano et al. | 360/8 |
| 4,646,722 A | 3/1987 | Silverstein et al. | 128/4 |
| 4,662,360 A | 5/1987 | O'Hara et al. | 128/9 |
| 4,733,063 A | 3/1988 | Kimura et al. | 250/201 |
| 4,741,326 A | 5/1988 | Sidall et al. | 128/4 |
| 4,753,530 A | 6/1988 | Knight et al. | 356/73 |
| 4,768,513 A | 9/1988 | Suzuki | 128/634 |
| 4,800,571 A | 1/1989 | Konishi | 375/10 |
| 4,844,617 A | 7/1989 | Kelderman et al. | 356/372 |
| 4,845,352 A | 7/1989 | Benschop | 250/201 |
| 4,852,955 A | 8/1989 | Doyle et al. | 350/1.2 |
| 4,877,033 A | 10/1989 | Seitz, Jr. | 128/660.05 |
| 4,878,485 A | 11/1989 | Adair | 128/6 |
| 4,891,829 A | 1/1990 | Deckman et al. | 378/4 |
| 4,930,516 A | 6/1990 | Alfano et al. | 128/665 |
| 4,945,478 A | 7/1990 | Merickel et al. | 364/413.22 |
| 4,965,441 A | 10/1990 | Picard | 250/201.3 |
| 4,972,258 A | 11/1990 | Wolf et al. | 358/93 |
| 4,974,580 A | 12/1990 | Anapliotis | 128/4 |
| 4,979,498 A | 12/1990 | Oneda et al. | 128/6 |
| 4,997,242 A | 3/1991 | Amos | 350/6.91 |
| 5,003,979 A | 4/1991 | Merickel et al. | 364/413.22 |
| 5,011,243 A | 4/1991 | Doyle et al. | 350/1.2 |
| 5,022,757 A | 6/1991 | Modell | 356/318 |
| 5,028,802 A | 7/1991 | Webb et al. | 250/571 |
| 5,032,720 A | 7/1991 | White | 250/236 |
| 5,034,613 A | 7/1991 | Denk et al. | 250/458.1 |
| 5,036,853 A | 8/1991 | Jeffcoat et al. | 128/634 |
| 5,042,494 A | 8/1991 | Alfano | 128/665 |
| 5,048,946 A | 9/1991 | Sklar et al. | 351/206 |
| 5,054,926 A | 10/1991 | Dabbs et al. | 356/345 |
| 5,065,008 A | 11/1991 | Hakamata et al. | 250/216 |
| 5,071,246 A | 12/1991 | Blaha et al. | 351/221 |
| 5,074,306 A | 12/1991 | Green et al. | 128/664 |
| 5,083,220 A | 1/1992 | Hill | 359/234 |
| 5,091,652 A | 2/1992 | Mathies et al. | 250/458.1 |
| 5,101,825 A | 4/1992 | Gravenstein et al. | 128/633 |
| 5,120,953 A | 6/1992 | Harris | 250/227.2 |
| 5,122,653 A | 6/1992 | Ohki | 250/216 |
| 5,132,526 A | 7/1992 | Iwasaki | 250/201.3 |
| 5,139,025 A | 8/1992 | Lewis et al. | 128/665 |
| 5,154,166 A | 10/1992 | Chikama | 128/4 |
| 5,159,919 A | 11/1992 | Chikama | 128/4 |
| 5,161,053 A | 11/1992 | Dabbs | 359/384 |
| 5,162,641 A | 11/1992 | Fountain | 250/201.2 |
| 5,162,941 A | 11/1992 | Favro et al. | 359/386 |
| 5,168,157 A | 12/1992 | Kimura | 250/234 |
| 5,192,980 A | 3/1993 | Dixon et al. | 356/326 |
| 5,193,525 A | 3/1993 | Silverstein et al. | 128/4 |
| RE34,214 E | 4/1993 | Carlsson et al. | 358/93 |
| 5,199,431 A | 4/1993 | Kittrell et al. | 128/634 |
| 5,201,318 A | 4/1993 | Rava et al. | 128/665 |
| 5,201,908 A | 4/1993 | Jones | 128/4 |
| 5,203,328 A | 4/1993 | Samuels et al. | 128/633 |
| 5,225,671 A | 7/1993 | Fukuyama | 250/216 |
| 5,235,457 A | 8/1993 | Lichtman et al. | 359/368 |
| 5,237,984 A | 8/1993 | Williams, III et al. | 128/4 |
| 5,239,178 A | 8/1993 | Derndinger et al. | 250/234 |
| 5,248,876 A | 9/1993 | Kerstens et al. | 250/561 |
| 5,253,071 A | 10/1993 | MacKay | 358/222 |
| 5,257,617 A | 11/1993 | Takahashi | 128/4 |
| 5,260,569 A | 11/1993 | Kimura | 250/234 |
| 5,260,578 A | 11/1993 | Bliton et al. | 250/461.1 |
| 5,261,410 A | 11/1993 | Alfano et al. | 128/664 |
| 5,262,646 A | 11/1993 | Booker et al. | 250/341 |
| 5,274,240 A | 12/1993 | Mathies et al. | 250/458.1 |
| 5,284,149 A | 2/1994 | Dhadwal et al. | 128/665 |
| 5,286,964 A | 2/1994 | Fountain | 250/201.2 |
| 5,289,274 A | 2/1994 | Kondo | 348/208 |
| 5,294,799 A | 3/1994 | Aslund et al. | 250/458.1 |
| 5,296,700 A | 3/1994 | Kumagai | 250/216 |
| 5,303,026 A | 4/1994 | Strobl et al. | 356/318 |
| 5,306,902 A | 4/1994 | Goodman | 250/201.3 |
| 5,313,567 A | 5/1994 | Civanlar et al. | 395/124 |
| 5,319,200 A | 6/1994 | Rosenthal et al. | 250/341 |
| 5,321,501 A | 6/1994 | Swanson et al. | 356/345 |
| 5,324,979 A | 6/1994 | Rosenthal | 250/504 R |
| 5,325,846 A | 7/1994 | Szabo | 128/4 |
| 5,329,352 A | 7/1994 | Jacobsen | 356/301 |
| 5,337,734 A | 8/1994 | Saab | 128/4 |
| 5,343,038 A | 8/1994 | Nishiwaki et al. | 250/234 |
| 5,345,306 A | 9/1994 | Ichimura et al. | 356/346 |
| 5,345,941 A | 9/1994 | Rava et al. | 128/665 |
| 5,349,961 A | 9/1994 | Stoddart et al. | 128/665 |
| 5,398,685 A | 3/1995 | Wilk et al. | 128/653.1 |
| 5,402,768 A | 4/1995 | Adair | 128/4 |
| 5,406,939 A | 4/1995 | Bala | 128/4 |
| 5,413,092 A | 5/1995 | Williams, III et al. | 128/4 |
| 5,413,108 A | 5/1995 | Alfano | 128/665 |
| 5,415,157 A | 5/1995 | Welcome | 128/4 |
| 5,418,797 A | 5/1995 | Bashkansky et al. | 372/3 |
| 5,419,311 A | 5/1995 | Yabe et al. | 128/4 |
| 5,419,323 A | 5/1995 | Kittrell et al. | 128/653 |
| 5,421,337 A | 6/1995 | Richards-Kortum et al. | 128/665 |
| 5,421,339 A | 6/1995 | Ramanujam et al. | 128/665 |
| 5,424,543 A | 6/1995 | Dombrowski et al. | 250/330 |
| 5,450,857 A | 9/1995 | Garfield et al. | 128/778 |
| 5,451,931 A | 9/1995 | Muller et al. | 340/630 |
| 5,458,132 A | 10/1995 | Yabe et al. | 128/4 |
| 5,458,133 A | 10/1995 | Yabe et al. | 600/121 |
| 5,467,767 A | 11/1995 | Alfano et al. | 128/665 |
| 5,469,853 A | 11/1995 | Law et al. | 128/662.06 |
| 5,477,382 A | 12/1995 | Pernick | 359/559 |
| 5,480,775 A | 1/1996 | Ito et al. | 435/7.2 |
| 5,493,444 A | 2/1996 | Khoury et al. | 359/559 |
| 5,496,259 A | 3/1996 | Perkins | 600/124 |
| 5,507,295 A | 4/1996 | Skidmore | 600/121 |
| 5,516,010 A | 5/1996 | O'Hara et al. | 600/122 |
| 5,519,545 A | 5/1996 | Kawahara | 360/46 |
| 5,529,235 A | 6/1996 | Boiarski et al. | 227/175.1 |
| 5,536,236 A | 7/1996 | Yabe et al. | 600/125 |
| 5,545,121 A | 8/1996 | Yabe et al. | 600/121 |
| 5,551,945 A | 9/1996 | Yabe et al. | 600/122 |
| 5,556,367 A | 9/1996 | Yabe et al. | 600/124 |
| 5,562,100 A | 10/1996 | Kittrell et al. | 128/665 |
| 5,579,773 A | 12/1996 | Vo-Dinh et al. | 128/665 |
| 5,582,168 A | 12/1996 | Samuels et al. | 128/633 |
| 5,587,832 A | 12/1996 | Krause | 359/385 |
| 5,596,992 A | 1/1997 | Haaland et al. | 128/664 |
| 5,599,717 A | 2/1997 | Vo-Dinh | 436/63 |
| 5,609,560 A | 3/1997 | Ichikawa et al. | 600/101 |
| 5,612,540 A | 3/1997 | Richards-Kortum et al. | 250/461.2 |
| 5,623,932 A | 4/1997 | Ramanujam et al. | 128/665 |
| 5,647,368 A | 7/1997 | Zeng et al. | 128/665 |
| 5,662,588 A | 9/1997 | Iida | 600/121 |
| 5,685,822 A | 11/1997 | Harhen | 600/125 |
| 5,690,106 A | 11/1997 | Bani-Hashemi et al. | 128/653.1 |
| 5,693,043 A | 12/1997 | Kittrell et al. | 606/15 |
| 5,695,448 A | 12/1997 | Kimura et al. | 600/121 |
| 5,697,373 A | 12/1997 | Richards-Kortum et al. | 128/664 |
| 5,699,795 A | 12/1997 | Richards-Kortum | 128/634 |
| 5,704,892 A | 1/1998 | Adair | 600/121 |
| 5,707,343 A | 1/1998 | O'Hara et al. | 600/121 |
| 5,713,364 A | 2/1998 | DeBaryshe et al. | 128/664 |
| 5,717,209 A | 2/1998 | Bigman et al. | 250/339.12 |
| 5,730,701 A | 3/1998 | Furukawa et al. | 600/127 |
| 5,733,244 A | 3/1998 | Yasui et al. | 600/127 |

| | | | |
|---|---|---|---|
| 5,735,276 A | 4/1998 | Lemelson et al. | 128/653 |
| 5,746,695 A | 5/1998 | Yasui et al. | 600/127 |
| 5,768,333 A | 6/1998 | Abdel-Mottaleb | 378/37 |
| 5,769,792 A | 6/1998 | Palcic et al. | 600/477 |
| 5,773,835 A | 6/1998 | Sinofsky | 250/462.1 |
| 5,791,346 A | 8/1998 | Craine et al. | 128/653 |
| 5,795,632 A | 8/1998 | Buchalter | 428/35.2 |
| 5,800,350 A | 9/1998 | Coppleson et al. | 600/372 |
| 5,807,248 A | 9/1998 | Mills | 600/322 |
| 5,813,987 A | 9/1998 | Modell et al. | 600/473 |
| 5,817,015 A | 10/1998 | Adair | 600/121 |
| 5,830,146 A | 11/1998 | Skladnev et al. | 600/478 |
| 5,833,617 A | 11/1998 | Hayashi | 600/476 |
| 5,840,035 A | 11/1998 | Heusmann et al. | 600/47 |
| 5,842,995 A | 12/1998 | Mahadevan-Jansen et al. | 600/473 |
| 5,855,551 A | 1/1999 | Sklandnev et al. | 600/372 |
| 5,860,913 A | 1/1999 | Yamaya et al. | 600/127 |
| 5,863,287 A | 1/1999 | Segawa | 600/121 |
| 5,865,726 A | 2/1999 | Katsurada et al. | 600/127 |
| 5,876,329 A | 3/1999 | Harhen | 600/125 |
| 5,920,399 A | 7/1999 | Sandison et al. | 356/418 |
| 5,921,926 A | 7/1999 | Rolland et al. | 600/407 |
| 5,929,985 A | 7/1999 | Sandison et al. | 365/318 |
| 5,931,779 A | 8/1999 | Arakaki et al. | 600/310 |
| 5,938,617 A | 8/1999 | Vo-Dinh | 600/476 |
| 5,941,834 A | 8/1999 | Skladnev et al. | 600/587 |
| 5,983,125 A | 11/1999 | Alfano et al. | 600/473 |
| 5,989,184 A | 11/1999 | Blair et al. | 600/167 |
| 5,991,653 A | 11/1999 | Richards-Kortum et al. | 660/475 |
| 5,995,645 A | 11/1999 | Soenksen et al. | 382/133 |
| 6,021,344 A | 2/2000 | Lui et al. | 600/476 |
| 6,058,322 A | 5/2000 | Nishikawa et al. | 600/408 |
| 6,069,689 A | 5/2000 | Zeng et al. | 356/773 |
| 6,091,985 A | 7/2000 | Alfano et al. | 600/476 |
| 6,095,982 A | 8/2000 | Richards-Kortum et al. | 600/476 |
| 6,096,065 A | 8/2000 | Crowley | 607/88 |
| 6,099,464 A | 8/2000 | Shimizu et al. | 600/104 |
| 6,104,945 A | 8/2000 | Modell et al. | 600/473 |
| 6,119,031 A | 9/2000 | Crowley | 600/407 |
| 6,124,597 A | 9/2000 | Shehada et al. | 250/461.2 |
| 6,146,897 A | 11/2000 | Cohenford et al. | 436/63 |
| 6,169,817 B1 | 1/2001 | Parker et al. | 382/131 |
| 6,208,887 B1 | 3/2001 | Clarke et al. | 600/476 |
| 6,241,662 B1 | 6/2001 | Richards-Kortum et al. | 600/310 |
| 6,243,601 B1 | 6/2001 | Wist | 600/473 |
| 6,246,471 B1 * | 6/2001 | Jung et al. | 356/73 |
| 6,246,479 B1 | 6/2001 | Jung et al. | 356/73 |
| 6,285,639 B1 | 9/2001 | Maenza et al. | 369/47.28 |
| 6,312,385 B1 | 11/2001 | Mo et al. | 600/443 |
| 6,317,617 B1 | 11/2001 | Gilhuijs et al. | 600/408 |
| D453,832 S | 2/2002 | Morrell et al. | D24/138 |
| D453,962 S | 2/2002 | Morrell et al. | D24/138 |
| D453,963 S | 2/2002 | Morrell et al. | D24/138 |
| D453,964 S | 2/2002 | Morrell et al. | D24/138 |
| 6,377,842 B1 | 4/2002 | Pogue et al. | 600/478 |
| 6,385,484 B2 | 5/2002 | Nordstrom et al. | 600/476 |
| 6,411,835 B1 | 6/2002 | Modell et al. | 600/407 |
| 6,411,838 B1 | 6/2002 | Nordstrom et al. | 600/476 |
| D460,821 S | 7/2002 | Morrell et al. | D24/138 |
| 6,421,553 B1 | 7/2002 | Costa et al. | 600/476 |
| 6,427,082 B1 * | 7/2002 | Nordstrom et al. | 600/476 |
| 6,571,118 B1 | 5/2003 | Utzinger et al. | 600/476 |
| 6,574,502 B2 | 6/2003 | Hayashi | 600/476 |
| 2001/0041843 A1 * | 11/2001 | Modell et al. | 600/473 |
| 2002/0007122 A1 * | 1/2002 | Kaufman et al. | 600/476 |
| 2002/0007123 A1 | 1/2002 | Balas et al. | 600/476 |
| 2002/0127735 A1 * | 9/2002 | Kaufman et al. | 436/172 |
| 2002/0133073 A1 * | 9/2002 | Nordstrom et al. | 600/426 |
| 2002/0177777 A1 * | 11/2002 | Nordstrom et al. | 600/475 |
| 2002/0183626 A1 * | 12/2002 | Nordstrom et al. | 600/476 |
| 2002/0197728 A1 * | 12/2002 | Kaufman et al. | 436/164 |
| 2003/0095721 A1 * | 5/2003 | Clune et al. | 382/294 |
| 2003/0144585 A1 * | 7/2003 | Kaufman et al. | 600/407 |
| 2003/0207250 A1 * | 11/2003 | Kaufman et al. | 435/4 |
| 2004/0007674 A1 * | 1/2004 | Schomacker et al. | 250/458.1 |
| 2004/0010187 A1 * | 1/2004 | Schomacker et al. | 600/317 |
| 2004/0010195 A1 * | 1/2004 | Zelenchuk | 600/476 |
| 2004/0010375 A1 * | 1/2004 | Schomacker et al. | 250/458.1 |
| 2004/0023406 A1 * | 2/2004 | Schomacker et al. | 436/164 |

FOREIGN PATENT DOCUMENTS

| | | |
|---|---|---|
| EP | 0 444 689 A2 | 9/1991 |
| EP | 0 474 264 | 3/1992 |
| EP | 0 641 542 | 3/1995 |
| EP | 0 689 045 A1 | 12/1995 |
| EP | 0 737 849 A2 | 10/1996 |
| JP | 08-280602 | 10/1996 |
| SU | 1 223 092 | 4/1986 |
| WO | WO 92/19148 | 11/1992 |
| WO | WO 93/14688 | 8/1993 |
| WO | WO 94/26168 | 11/1994 |
| WO | WO 95/00067 | 1/1995 |
| WO | WO 95/04385 | 2/1995 |
| WO | WO 97/05473 | 2/1997 |
| WO | WO 98/30889 | 2/1997 |
| WO | WO 97/48331 | 12/1997 |
| WO | WO 98/05253 | 2/1998 |
| WO | WO 98/24369 | 6/1998 |
| WO | WO 98/41176 | 9/1998 |
| WO | WO 99/18847 | 4/1999 |
| WO | WO 99/20313 | 4/1999 |
| WO | WO 99/20314 | 4/1999 |
| WO | WO 99/47041 | 9/1999 |
| WO | WO 99/57507 | 11/1999 |
| WO | WO 99/57529 | 11/1999 |
| WO | WO 00/15101 | 3/2000 |
| WO | WO 00/59366 | 10/2000 |

OTHER PUBLICATIONS

Balas (1997), "An Imaging Colorimeter for Noncontact Tissue Color Mapping," *IEEE Transactions on Biomedical Engineering,* 44(6):468–474.

Balas (2001), "A Novel Optical Imaging Method for the Early Detection, Quantitative Grading, and Mapping of Cancerous and Precancerous Lesions of Cervix," *IEEE Transactions on Biomedical Engineering,* 48(1):96–104.

Balas et al. (1997), "A modular diffuse reflection and fluorescence emission imaging colorimeter for the in–vivo study of parameters related with the phototoxic effect in PDT," *SPIE,* 3191:50–57.

Balas et al. (1998), "In Vivo Assessment of Acetic Acid–Cervical Tissue Interaction Using Quantitative Imaging of Back–Scattered Light: Its Potential Use for the In Vivo Cervical Cancer Detection Grading and Mapping," Part of EUROPTO Conference on Optical Biopsy, Stockholm Sweden, *SPIE,* vol. 3568:31–37.

Balas et al. (1999), "In Vivo Detection and Staging of Epithelial Dysplasias and Malignancies Based on the Quantitative Assessment of Acetic Acid–Tissue Interaction Kinetics," *Journal of Photochemistry and Photobiology B: Biology,* 53:153–157.

Bessey et al. (1949), "The Fluorometic measurement of the nucleotides of riboflavin and their concentration in tissues," *J. Biol.–Chem.;* 180:755–769.

Bors et al. (1988), "Optical flow estimation and moving object segmentation based on median radial basis function network," *IEEE Transactions on Image Processing,* 7(5):693–702.

Boutheny et al. (1999), "A unified approach to shot change detection and camera motion characterization," *IEEE Transactions on Circuits and Systems for Video Technology,* 9(7):1030–1044.

Braichotte et al. (1995), "Clinical Pharmacokinetic Studies of Photofrin by Fluorescence Spectroscopy in the Oral Cavity, the Esophagus, and the Bronchi," *Cancer* 75(11):2760–2778.

Brown (1990), "Chemometrics," *Anal. Chem.,* 62:84R–101R.

Camus et al. (1997), "Real–time quantized optical flow," *Real–Time Imaging,* 3:71–86.

Caplier et al. (1998), "Real–time implementation of a MRF–based motion detection algorithm," *Real–time Imaging,* 4:41–54.

Contini et al. (1989), "Colposcoy and Computer Graphics: a New Method?" *Amer. J. Obstet. Gynecol.,* 160(3):535–538.

Craine et al. (1993), "Digital Imaging Colposcopy: basic concepts and applications," *Amer. J. Obstet. Gynecol.,* 82(5):869–873.

Craine et al. (1998), "Digital imaging colposcopy: Corrected area measurements using shape–from–shading," *IEEE Transactions on Medical Imaging,* 17(6):1003–1010.

Crisp et al. (1990), "The Computerized Digital Imaging Colposcope: Future Directions," *Amer. J. Obstet. Gynecol.,* 162(6):1491–1497.

Cronjé et al. (1997), "Effects of Dilute Acetic Acid on the Cervical Smear," *Acta. Cytol.,* 41:1091–1094.

Dickman et al. (2001), "Identification of Cervical Neoplasia Using a Simulation of Human Vision," *Journal of Lower Genital Tract Disease,* 5(3):144–152.

Drezek et al. (1999), "Light scattering from cells: finite–difference time–domain simulations and goniometric measurements," *Applied Optics* 38(16):3651–3661.

Drezek et al. (2000), "Laser Scanning Confocal Microscopy of Cervical Tissue Before and After Application of Acetic Acid," *Am. J. Obstet. Gynecol.,* 182(5):1135–1139.

Dumontier et al. (1999), "Real–time DSP implementation for MRF–based video motion detection," *IEEE Transactions on Image Processing,* 8(10):1341–1347.

Earnshaw et al. (1996), "The Performance of Camera Translation Direction Estimators from Optical Flow: Analysis, Comparison and Theoretical Limits," *IEEE Transactions on Pattern Analysis and Machine Intelligence,* 18(9):927–932.

Edebiri, A.A. (1990), "The relative significance of colposcopic discriptive appearances in the dianosis of cervical intraepithelial neoplasia," *Int. J. Gynecol. Obstet.,* 33:23–29.

Eisner et al. (1987), "Use of Cross–Correlation Function to Detect Patient Motion During Spectral Imaging," *Journal of Nuclear Medicine,* 28(1):97–101.

Ferris et al. (1998), "Colposcopy Quality Control: Establishing Colposcopy Criterion Standards for the NCI ALTS Trial Using Cervigrams," *J. Lower Genital Tract Disease,* 2(4):195–203.

Fleet et al. (1995), "Recursive Filters for Optical Flow," *IEEE Transactions on Pattern Analysis and Machine Intelligence,* 17(1):61–67.

Gao et al. (1998), "A work minimization approach to image morphing," *The Visual Computer,* 14:390–400.

Gauch (1999), "Image Segmentation and Analysis Via Multiscale Gradient Watershed Hierarchies," *IEEE Transaction on Image Processing,* 8(1):69–79.

Haralick (1984), "Digital Step Edges from Zero Crossing of Second Directional Derivatives," *IEEE Transactions on Pattern Analysis and Machine Intelligence,* 6(1):58–68.

Haris et al. (1998), "Hybrid Image Segmentation Using Watersheds and Fast Region Merging," *IEEE Transactions on Image Processing,* 7(12):1684–1699.

Helmerhorst et al. (1987), "The accuracy of colposcopically directed biopsy in diagnosis of CIN 2/3." *Eur. J. Obstet. Gyn. Reprod. Biol.,* 24, 221–229.

Horn et al. (1981), "Determining Optical Flow," *Artificial Intelligence,* 17(1–3):185–203.

Horn et al. (1993), "Determining Optical Flow,": a retrospective, *Artificial Intelligence,* 59:81–87.

Huang et al. (1979), "A fast two–dimensional median filtering algorithm," *IEEE Transactions on Acoustics, Speech, and Signal Processing,* 27(1):13–18.

Jackway (1996), "Gradient Watersheds in Morphological Scale–Space," *IEEE Transactions on Image Processing,* 5(6):913–921.

Ji et al. (2000), "Texture Analysis for Classification of Cervix Lesions," *IEEE Transactions on Medical Imaging,* 19(11):1144–1149.

Kierkegaard et al. (1995), "Association between Colposcopic Findings and Histology in Cervical Lesions: the Significance of the Size of the Lesion" *Gynecologic Oncology,* 57:66–71.

Kumar et al. (1996), "Optical Flow: A Curve Evolution Approach," *IEEE Transactions on Image Processing,* 5(4):598–610.

Linde et al. (1980), An algorithm for vector quantizer design,: *IEEE Transactions on Communications,* 28(1):84–95.

MacAulay et al. (2002), "Variation of fluorescence spectroscopy during the menstrual cycle," *Optics Express,* 10(12):493–504.

MacLean A.B. (1999), "What is Acetowhite Epithelium," *Abstract Book: 10$^{th}$ World Congress of Cervical Pathology and Colposcopy,* Nov. 7–11, Buenos Aires, Argentina 41.

Marzetta et al. (1999), "A surprising radon transform result and its application to motion detection," *IEEE Transactions on Image Processing,* 8(8):1039–1049.

Miike et al. (1999), "Motion enhancement for preprocessing of optical flow and scientific visualization," *Pattern Recognition Letters,* 20:451–461.

Mikhail et al. (1995), "Computerized colposcopy and conservative management of cervical intraepithelial neoplasia in pregnancy," *Acta Obstet. Gynecol. Scand.,* 74:376–378.

Milanfar (1999), "Two–dimensional matched filtering for motion estimation," *IEEE Transactions on Image Processing,* 8(3):438–444.

Mitchell et al. (1998), "Colposcopy for the diagnosis of squamous intraepithelial lesions: a meta–analysis," *Obstet. Gynecol.,* 91(4):626–631.

Mycek et al. (1998), "Colonic polyp differentiation using time–resolved autofluorescence spectroscopy," *Gastrointestinal Endoscopy,* 48(4):390–394.

Nanda et al. (2000), "Accuracy of the Papanicolaou test in screening for and follow–up of cervical cytologic abnormalities: a systematic review," *Ann Intern Med.,* 132(10):810–819.

Nesi et al. (1998), "RETIMAC REalTIme Motion Analysis Chip," *IEEE Transactions on Circuits and Systems–II: Analog and Digital Signal Processing*, 45(3):361–375.

Nourneir et al. (1996), "Detection of Motion During Tomographic Acquisition by an Optical Flow Algorithm," *Computers and Biomedical Research*, 29(1):1–15.

O'Sullivan et al. (1994), "Interobserver variation in the diagnosis and grading of dyskaryosis in cervical smears: specialist cytopathologists compared with non–specialists," *J. Clin. Pathol.*, 47(6):515–518.

Ogura et al. (1995), "A cost effective motion estimation processor LSI using a simple and efficient algorithm," *IEEE Transactions on Consumer Electronics*, 41(3):690–698.

Okatani et al. (1997), "Shape reconstruction from an endoscope image by shape from shading technique for a point light source at the projection center," *Computer Vision and Image Understanding*, 66(2):119–131.

Pan et al. (1998), "Correlation–feedback Technique in Optical Flow Determination," *IEEE Transactions on Image Processing*, 7(7):1061–1067.

Perona et al. (1990), "Scale–space and edge detection using anisotropic diffusion," *IEEE Transactions on Pattern Analysis and Machine Intelligence*, 12(7):629–639.

Pogue et al. (2001), "Analysis of Acetic Acid–Induced Whitening of High–Grade Squamous Intraepithelial Lesions," *Journal of Biomedical Optics*, 6(4):397–403.

Radjadhyaksha et al. (2000), "Confocal microscopy of excised human skin using acetic acid and crossed polarization: rapid detection of non–melanoma skin cancers," *Proceedings of SPIE*, 3907:84–88.

Rakshit et al. (1997), "Computation of Optical Flow Using Basis Functions," *IEEE Transactions on Image Processing*, 6(9):1246–1254.

Reid et al. (1985), "Genital warts and cervical cancer. VII. An improved colposcopic index for differentiating benign papillomaviral infections from high–grade CIN," *Am. J. Obstet. Gynecol.*, 153(6):611–618.

Romano et al. (1997), "Spectroscopic study of human leukocytes," *Physica Medica*, 13:291–295.

Ruprecht et al. (1995), "Image warping with scattered data interpolation methods," *IEEE Computer Graphics and Applications*, 37–43.

Sakuma (1985), "Quantitative Analysis of the Whiteness of the Atypical Cervical Transformation Zone", *The Journal of Reproductive Medicine*, 30(10):773–776.

Schmid (1999), "Lesion Detection in Dermatoscopic Images Using Anisotropic Diffusion and Morphological Flooding," *Proceedings of the International Conference on Image Processing (ICIP–99)*, 3:449–453.

Schmid (1999), "Segmentation and Symmetry Measure for Image Analysis: Application to Digital Dermatoscopy," *Ph.D. Thesis, Swiss Federal Institute of Technology (EPFL). Signal Processing Laboratory (LTS)*.

Schmid (1999), "Segmentation of Digitized Dermatoscopic Images by 2D Color Clustering," *IEEE Transactions on Medical Imaging*, 18(2):164–171.

Schomacker et al. (1992), "Ultraviolet Laser–Induced Fluorescence of Colonic Polyps," *Gastroenterology*, 102:1155–1160.

Shafarenko et al. (1997), "Automatic Watershed Segmentation of Randomly Textured Color Images," *IEEE Transactions on Image Processing*, 6(11):1530–1544.

Shafi et al. (1995), "Modern image capture and data collection technology," *Clin. Obstet. Gynecol.*, 38(3):640–643.

Szarewski et al., (1996), "Effect of smoking cessation on cervical lesions size," *Lancet*, 347:941–943.

Szeliski et al. (1997), "Spline–based image registration," *International Journal of Computer Vision*, 22(3):199–218.

Tadrous (2000), "Methods for Imaging the Structure and Function of Living Tissues and Cells: 2. Fluorescence Lifetime Imaging," *Journal of Pathology*, 191(3):229–234.

Thirion et al. (1999), "Deformation analysis to detect and quantify active lesions in three–dimensional medical image sequences," *IEEE Transactions on Medial Imaging*, 18(5):429–441.

Toglia et al. (1997), "Evaluation of colposcopic skills in an obstetrics and gynecology residency training program," *J. Lower Gen. Tract. Dis.*, 1(1):5–8.

Treameau et al. (1997), "A Region Growing and Merging Algorithm to Color Segmentation," *Pattern Recognition*, 30(7):1191–1203.

Van den Elsen et al. (1995), "Automatic registration of ct and mr brain images using correlation of geometrical features," *IEEE Transactions on medical imaging*, 14(2):384–396.

Vernon (1999), "Computation of Instantaneous Optical Flow Using the Phase of Fourier Components," *Image and Vision Computing*, 17:189–199.

Vincent et al. (1991), "Watersheds in Digital Spaces: An Efficient Algorithm Based on Immersion Simulations," *IEEE Transactions on Patterns Analysis and Machine Intelligence*, 13(6):583–598.

Vincent et al. (1993), "Morphological grayscale reconstruction in image analysis: Applications and eficient algorithms," *IEEE Transactions on Image Processing*, 2(2):176–201.

Wang et al. (1999), "Fast algorithms for the estimation of motion vectors," *IEEE Transactions on Image Processing*, 8(3):435–438.

Weng et al. (1997), "Three–Dimensional Surface Reconstruction Using Optical Flow for Medical Imaging," *IEEE Transaction on Medical Imaging*, 16(5):630–641.

Wolberg et al. (1998) "Image morphing: a survey," *The Visual Computer*, 14:360–372.

You et al. (1996), "Behavioral analysis of anisotropic diffusion in image processing," *IEEE Transactions on Image Processing*, 5(11):1539–1553.

Zahm et al. (1998), "Colposcopic appearance of cervical intraepithelial neoplasia is age dependent," *Am. J. Obstet. Gynecol.*, 179(5):1298–1304.

Zeger et al. (1992), "Globally optimal vector quantizer design by stochastic relaxation," *IEEE Transactions on Signal Processing*, 40(2):310–322.

Zeng et al. (1993), "A computerized autofluorescence and diffuse reflectance spectroanalyser system for in vivo skin studies," *Phys. Med. Biol.*, 38:231–240.

Zeng et al. (1997), "Optimization of fast block motion estimation algorithms," *IEEE Transactions on Circuits and Systems for Video Technology*, 7(6):833–844.

Zhang et al. (1999), "Shape from shading: a survey," *IEEE Transactions on Pattern Analysis and Machine Intelligence*, 21(8):690–706.

Zheng et al. (1991), "Estimation of illumination direction, albedo, and shape from shading," *IEEE Transactions on Pattern Analysis and Machine Intelligence*, 13(7):680–702.

Zhengfang et al. (1998), "Identification of Colonic Dysplasia and Neoplasia by Diffuse Reflectance Spectroscopy and Pattern Recognition Techniques," *Applied Spectroscopy,* 52(6):833–839.

Nordstrom et al., 09/591,706, Jun. 9, 2000.

Modell et al., 09/481,762, Jan. 11, 2000.

Flewelling et al., 10/418,922, Apr. 18, 2003.

Jiang et al., 10/418,902, Apr. 18, 2003.

Costa et al., 10/418,686, Apr. 18, 2003.

Jiang et al., 10/481/975, Apr. 18, 2003.

Jiang et al., 10/419,181, Apr. 18, 2003.

Jiang, 10/418,974, Apr. 18, 2003.

Schomacker et al., 10/418,973, Apr. 18, 2003.

P. Davidovits et al. "Scanning Laser Microscope for Biological Investigations", Applied Optics, vol. 10, No. 7, pp. 1615–1619, Jul. 1971.

C.J.R. Sheppard et al. "Depth of Field in the Scanning Microscope", Optics Letters, vol. 3, No. 3, Sep. 1978, pp. 115–117.

C.J. Koester, "Scanning Mirror Microscope with Optical Sectioning Characteristics: Applications in Ophthalmology", Applied Optics. vol. 19, No. 11, Jun. 1980, pp. 1749–1757.

Jeffrey W. Hall, et al. "Near–Infrared Spectrophotometry: A New Dimension in Clinical Chemistry", Clin. Chem 38/9, 1623–1631 (1992).

Kevin T. Schomacker et al. "Ultraviolet Laser–Induced Fluorescence of Colonic Tissue; Basic Biology and Diagnostic Potential", Lasers in Surgery and Medicine, 12: 63–78, (1992).

S. Schwartz, "Real–time laser–scanning Confocal ratio imaging", American Laboratory, pp. 53–62 Apr. 1993.

R. Richards–Kortum et al. Description and Performance of a Fiber–optic Confocal Fluorescence Spectrometer, Applied Spectroscopy, vol. 48, No. 3 pp. 350–355. (1994).

J.M. Schmitt et al. "Interferometric Versus Confocal Techniques for Imaging Microstructures in Turbid Biological Media", Proc. SPIE, 2135 (1994), pp. 1–12.

N. Ramanujam et al. Fluorescence Spectroscopy; A Diagnostic Tool for Cervical Intraepithelial Neoplasia (CIN), Gynecologic Oncology 52, pp. 31–38 (1994).

S. G. Anderson, "Confocal Laser Microscopes See A Wider Filed of Application", Laser Focus World, pp. 83–86, Feb. 1994.

J.M. Schmitt et al. "Confocal Microscopy in Turbid Media", J. Opt. Soc. Am., vol. 11, pp. 2225–2235, Aug. 1994.

N. Ramanujam et al. "In vivo diagnosis of cervical intraepithelial neoplasia using 337–nm–exited laser–induced fluorescence", Pro Natl. Acad. Sci. USA, vol. 91, pp. 10193–10197, Oct. 1994.

* cited by examiner

SYSTEM FOR NORMALIZING SPECTRA

CROSS-REFERENCE TO RELATED APPLICATIONS

This application is related to the U.S. patent application entitled, "Spectral Data Classification of Samples" and identified by U.S. Ser. No. 09/738,481 (now U.S. Pat. No. 6,421,553), filed on even date herewith (Dec. 15, 2000), and the U.S. patent application entitled, "A Spectroscopic System Employing A Plurality of Data Types" and identified by U.S. Ser. No. 09/738,613 (now U.S. Pat. No. 6,385,484), filed on even date herewith (Dec. 15, 2000). All of the above applications are assigned to the common assignee of this application, and are hereby incorporated by reference.

GOVERNMENT RIGHTS

This invention was made with government support under Contract No. CA66481 awarded by National Cancer Institute, NIH. The government may have certain rights in the invention.

FIELD OF THE INVENTION

This invention relates generally to spectral analysis. More particularly, in one embodiment, the invention relates to analysis of optical spectra using only a portion of the spectral information for data normalization.

BACKGROUND OF THE INVENTION

In general, spectra are recorded as values of amplitude, typically measured as a response to an excitation, as a function of wavelength (or the inverse of wavelength, namely frequency). In the field of spectral analysis, it is often necessary to calibrate or preprocess one or more spectra in order to be able to compare spectra or to extract information from spectra. One calibration or preprocessing approach is to normalize a spectrum or a set of spectra. Normalization may be required, for example, when comparing spectra having different amplitudes. In the case of optical spectra in particular, differences in amplitude may result from differences in a level of illumination, differences in a response of a detector, or differences in optical behavior of one sample as compared to another. Normalization is a process whereby the differences in instrument performance from spectrum to spectrum are reduced or eliminated.

Two common methods for normalizing spectral information are to normalize a spectrum to a maximum value of amplitude in the spectrum ("peak normalization"), and to normalize a spectrum to an area determined by integrating the spectrum over a range of wavelengths or frequencies ("area normalization"). Peak normalization is performed by dividing the amplitude at each point in a spectrum by the maximum amplitude of that individual spectrum. One obtains a normalized spectrum having intensities ranging from 1.0 at the location of the maximum to possibly as little as 0.0 where the spectral amplitude vanishes. Peak normalization in principle removes the variations in instrument behavior from spectrum to spectrum. However, peak normalization discards information about differences in samples that cause differences in amplitude of response to an invariant excitation. Such information can be very useful, but it is eliminated by normalizing all spectra in a set to a common maximum normalized amplitude of 1.0.

Peak normalization is based on a single amplitude value that appears in a spectrum. To the extent that this single value is incorrect, through a change in illumination intensity, instrumental misalignment, excessive noise in the data, or the like, the peak normalization method will give erroneous information.

Area normalization is another method of normalizing spectra in which the area under the spectrum is computed, for example by integrating the amplitude of the spectrum as a function of wavelength or frequency, and the entire spectrum is recomputed by dividing each value of amplitude by the value determined for the area. The resulting area normalized spectrum has an area of one area unit. However, the energy carried by electromagnetic radiation is proportional to the frequency, v, of the radiation (e.g., Energy=hv), or equivalently, is inversely proportional to wavelength, λ, (i.e., Energy=hc/λ), where h is Planck's constant, and c is the speed of light. Therefore, an integration of amplitude over wavelength applies an equal "weight" to a unit of amplitude at long wavelength (i.e., low energy) as a unit of amplitude at short wavelength (i.e., high energy), even though one region may have a far different influence or effect than another, based on the energy content of the radiation.

SUMMARY OF THE INVENTION

The invention overcomes the disadvantages of the normalization methods that exist in the prior art, and provides an improved method and system for normalizing spectra. Rather than depending on a single observation, or on the entire range of observations, in a spectrum, in one embodiment, the invention uses as a basis for normalizing the spectrum, the range or ranges of observations within the spectrum that correspond to meaningful content in the spectrum. In one embodiment, the process of the invention is referred to as non-uniform segment normalization because it relies on the use of one or more segments of a spectrum that are not constrained to be of uniform width within the spectrum, nor do the observations have to be evenly spaced in wavelength across the entire spectrum.

In one aspect, the invention features a method of performing spectral analysis. The method includes obtaining an optical spectrum, and normalizing the optical spectrum by application of non-uniform segment normalization. In one embodiment, the method further includes selecting one or more segments from the optical spectrum, each of the segments being bounded by an upper wavelength and a lower wavelength and containing one or more wavelengths, each of the wavelengths having an associated amplitude; determining an area under a curve associated with each particular segment, wherein each the curve is bounded along a first axis by the upper wavelength and the lower wavelength of the particular segment, and along a second axis by the amplitudes associated with each of the wavelengths included in the particular segment; summing the areas for each of the segments to determine a normalization factor; and dividing at least one associated amplitude for one of the wavelengths included in the segments by the normalization factor.

In one embodiment, a first segment differs in size of wavelength range from that of a second segment, wherein the size of wavelength range is defined as the absolute magnitude of a difference between the upper wavelength and the lower wavelength. In another embodiment, a first segment is equal in wavelength range to a second segment.

In one embodiment, the one or more segments comprises at least first and second non-contiguous segments. In another embodiment, the one or more segments comprises at least first, second and third segments, and there exists a first span between an upper wavelength of the first segment and a lower wavelength of the second segment, and a second span between an upper wavelength of the second segment and a lower wavelength of the third segment. In one embodiment, the first and the second spans differ in magnitude. In an alternative embodiment, the first and the second spans are substantially equal in magnitude.

In one embodiment, the method further comprises obtaining the spectrum from a specimen of human cervical tissue. In another embodiment, the method further comprises extracting a test parameter from the optical spectrum. In still another embodiment, the method further comprises determining a disease status of the test specimen by analyzing the optical spectrum subsequent to the normalizing.

In another aspect, the invention features a system for performing spectral analysis. The system includes a spectrographic device, adapted to obtain an optical spectrum from a test specimen, and a processor adapted to normalize the optical spectrum by application of non-uniform segment normalization.

In one embodiment, the system further includes machine readable instructions executing on the processor and adapted to select one or more segments from the optical spectrum, each of the segments being bounded by an upper wavelength and a lower wavelength, and containing one or more wavelengths, each of the wavelengths having an associated amplitude; determine an area under a curve associated with each particular one of the segments, wherein each the curve is bounded along a first axis by the upper wavelength and the lower wavelength of the particular segment, and along a second axis by the amplitudes associated with each of the wavelengths included in the particular segment; sum the areas for each of the segments to determine a normalization factor; and divide at least one the associated amplitude for one of the wavelengths included in the segments by the normalization factor.

In one embodiment, the machine readable instructions are further adapted to one of select and enable a user to select a first segment different in size of wavelength range from that of a second segment, wherein the size of wavelength range is defined as the absolute magnitude of a difference between the upper wavelength and the lower wavelength. In another embodiment, the machine readable instructions are further adapted to one of select and enable a user to select a first segment to be substantially equal in size of wavelength range to that of a second segment. In still another embodiment, the machine readable instructions are further adapted to one of select and enable a user to select the one or more segments to include at least first and second non-contiguous segments. In yet another embodiment, the machine readable instructions are further adapted to one of select and enable a user to select the one or more segments to include at least first, second and third segments, and there exists a first wavelength span between an upper wavelength of the first segment and a lower wavelength of the second segment, and a second wavelength span between an upper wavelength of the second segment and a lower wavelength of the third segment. In one embodiment, the first and the second spans differ in magnitude. In an alternative embodiment, the first and the second spans are substantially equal in magnitude.

In another embodiment, the spectrographic device is further adapted to obtain the optical spectrum from a specimen of human cervical tissue. In another embodiment, the machine readable instructions are further adapted to extract a test parameter from the optical spectrum. In yet another embodiment, the machine readable instructions are further adapted to determine a disease status of the test specimen by analyzing the optical spectrum, subsequent to the normalizing.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

The invention will be described in terms of embodiments that relate to the normalization of optical spectra, particularly in the area of medical diagnostics, and especially as it relates to the analysis of spectra obtained from human cervical tissue in the detection of cervical cancer. However, the invention has applicability generally in the area of normalization of optical spectra.

Figure 1:
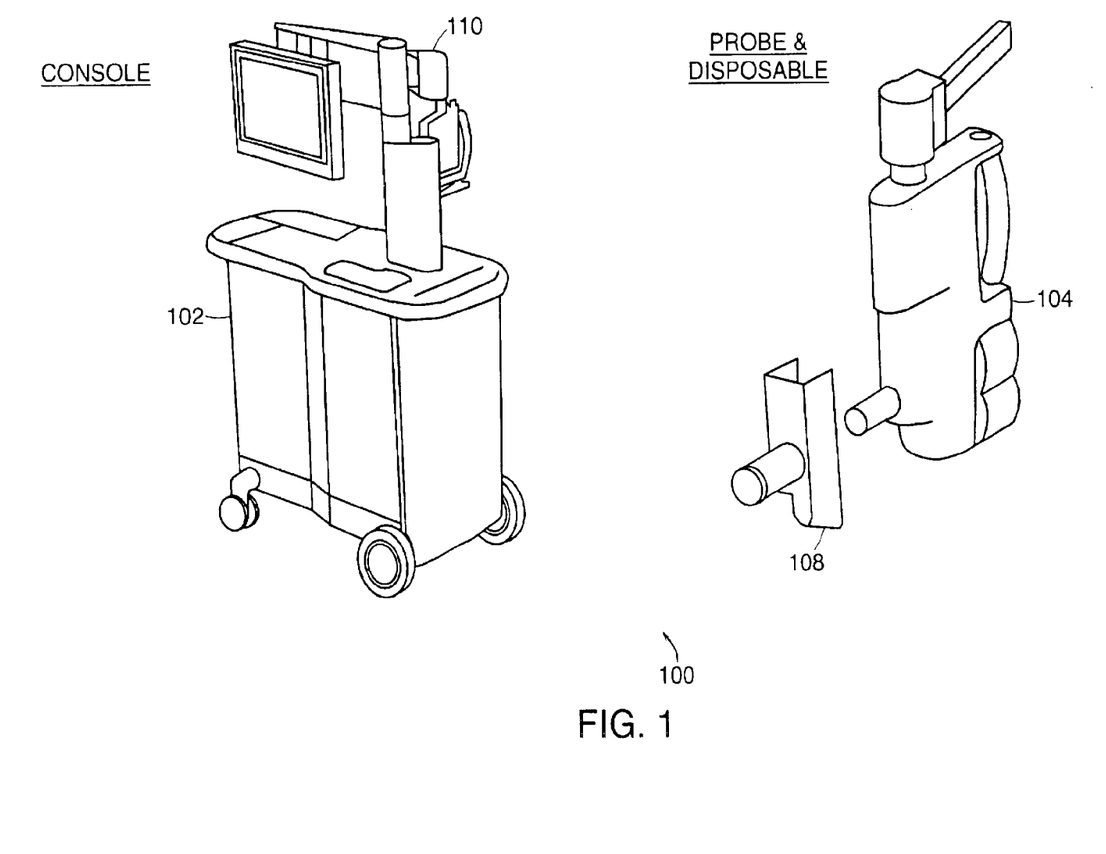
FIG. 1 shows an exemplary spectroscopic system employing a non-uniform segment normalization method according to an illustrative embodiment of the invention.
Figure 2:
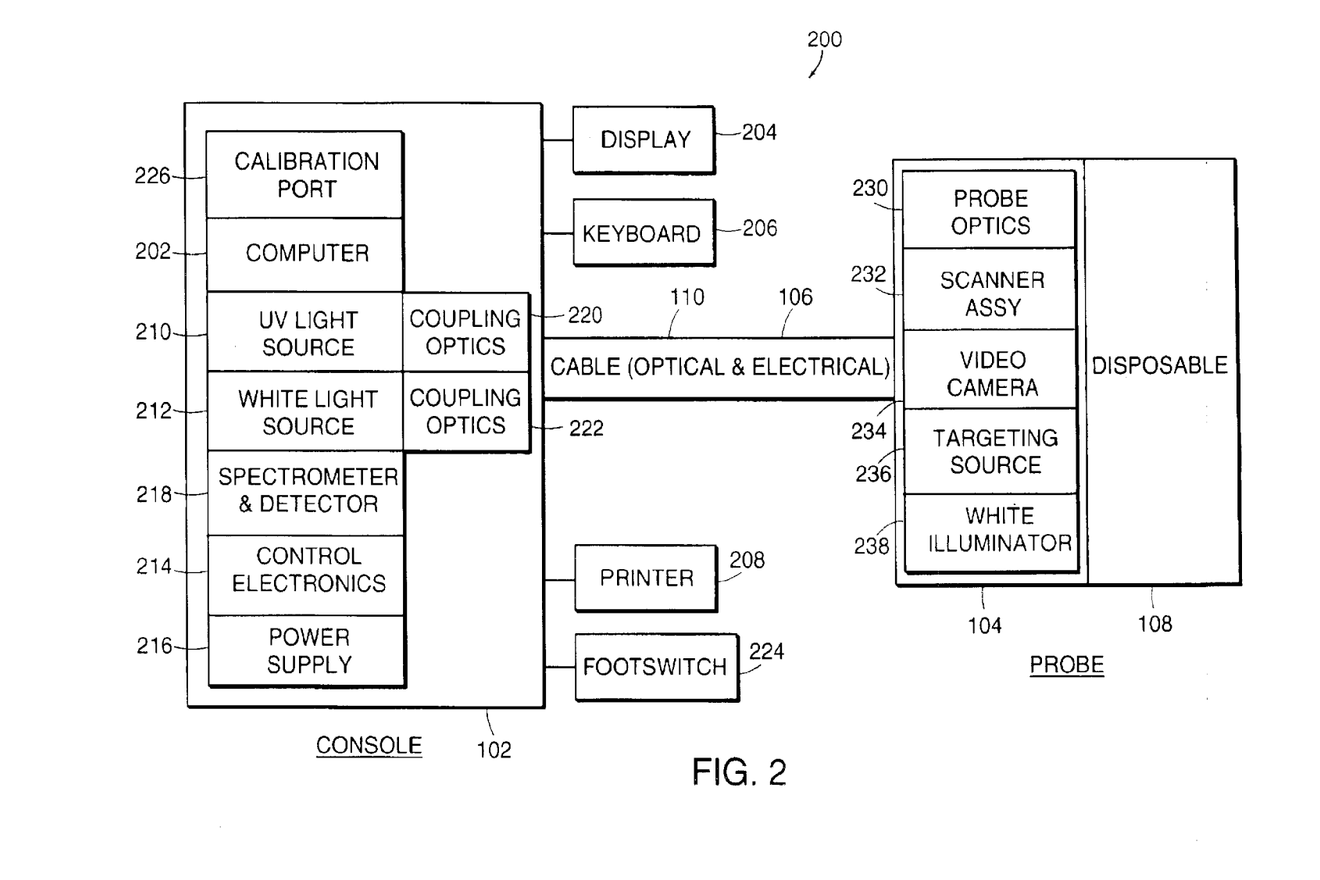
FIG. 2 shows an exemplary operational block diagram of the spectroscopic system of FIG. 1.

FIG. 1 depicts an exemplary spectroscopic system 100 employing a non-uniform segment normalization method according to an illustrative embodiment of the invention. The spectroscopic system includes a console 102 connected to a probe 104 by way of a cable 106, that is depicted in FIG. 2. The cable 106 carries electrical and optical signals between the console 102 and the probe 104. The probe 104 accommodates a disposable component 108 which used only once, and discarded after such use. In one embodiment, the console 102 and the probe 104 are mechanically connected by an articulating arm 110, which can also support the cable 106. The console 102 contains much of the hardware and the software of the system, and the probe 104 contains the necessary hardware for making suitable spectroscopic observations. The details of the system are further explained in conjunction with FIG. 2.

FIG. 2 shows an exemplary operational block diagram 200 of a spectroscopic system of the type depicted in FIG. 1. The spectroscopic system is similar to single-beam spectrometer devices, but is adapted to include the features of the invention. The console 102 includes a computer 202 which executes runs software that controls the operation of the spectroscopic system 100. The software includes one or more modules recorded on machine-readable media, which can be any medium such as magnetic disks, magnetic tape, CD-ROM, semiconductor memory, or the like. Preferably, the machine-readable medium is resident within the computer 202. In alternative embodiments, the machine-readable medium can be connected to the computer 202 by a communication link. In alternative embodiments, one can substitute computer insructions in the form of hardwired logic for software, or one can substitute firmware (i.e., computer instructions recorded on devices such as PROMs, EPROMS oe EEPROMs, or the like) for software. The term machine -readable instructions as used herein is intended to encompass software, hardwired logic, firmware and the like.

The computer 202 is a general purpose computer. The computer 202 can be an embedded computer, or a personal computer such as a laptop or desktop computer, that is capable of running the software, issuing suitable control commands, and recording information in real time. The computer 202 has a display 204 for reporting information to an operator of the spectroscopic system 100, a keyboard 206 for enabling the operator to enter information and commands, and a printer 208 for providing a print-out, or permanent record, of measurements made by the spectroscopic system 100 and for printing diagnostic results, for example, for inclusion in the chart of a patient. As described below in more detail, in an illustrative embodiment of the invention, some commands entered at the keyboard, enable a user to select particular segments of a spectrum for normalization. Other commands enable a user to select the wavelength range for each particular segment and to specify both wavelength contiguous and non-contiguous segments.

The console 102 also includes an ultraviolet (UV) source 210 such as a nitrogen laser or a frequency-tripled Nd:YAG laser, a white light source 212 such as one or more Xenon flash lamps, and control electronics 214 for controlling the light sources both as to intensity and as to the time of onset of operation and the duration of operation. One or more power supplies 216 are included in the console 102, to provide regulated power for the operation of all of the components. The console 102 also includes at least one spectrometer and at least one detector (spectrometer and detector 218) suitable for use with each of the light sources. In some embodiments, a single spectrometer can operate with both the UV light source and the white light source. In some embodiments, the same detector can record UV and white light signals, and in some embodiments different detectors are used for each light source.

The console 102 also includes coupling optics 220 to couple the UV illumination from the UV light source 210 to one or more optical fibers in the cable 106 for transmission to the probe 104, and for coupling the white light illumination from the white light source 212 to one or more optical fibers in the cable 106 for transmission to the probe 104. The console 102 also includes coupling optics 222 to couple the spectral response of a specimen to UV illumination from the UV light source 210 observed by the probe 104 and carried by one or more optical fibers in the cable 106 for transmission to the spectrometer and detector 218, and for coupling the spectral response of a specimen to the white light illumination from the white light source 212 observed by the probe 104 and carried by one or more optical fibers in the cable 106 for transmission to the spectrometer and detector 218. The console 102 includes a footswitch 224 to enable an operator of the spectroscopic system 100 to signal when it is appropriate to commence a spectral observation by stepping on the switch. In this manner, the operator has his or her hands free to perform other tasks, for example, aligning the probe 104.

The console 102 includes a calibration port 226 for calibrating the optical components of the spectrometer system. The operator places the probe 104 in registry with the calibration port 226 and issues a command that starts the calibration operation. In the calibration operation, a calibrated light source provides illumination of known intensity as a function of wavelength as a calibration signal. The probe 104 detects the calibration signal. The probe 104 transmits the detected signal through the optical fiber in the cable 106, through the coupling optics 222 to the spectrometer and detector 218. A test spectral result is obtained. A calibration of the spectral system is computed as the ratio of the amplitude of the known illumination at a particular wavelength divided by the test spectral result at the same wavelength.

The probe 104 includes probe optics 230 for illuminating a specimen to be analyzed with UV and white light from the UV source 210 and the white light source 212, and for collecting the fluorescent and backscatter illumination from the specimen that is being analyzed. The probe includes a scanner assembly 232 that provides illumination from the UV source 210 in a raster pattern over a target area of the specimen of cervical tissue to be analyzed. The probe includes a video camera 234 for observing and recording visual images of the specimen under analysis. The probe 104 includes a targeting source 236, which can be used to determine where on the surface of the specimen to be analyzed the probe 104 is pointing. The probe 104 also includes a white light illuminator 238 to assist the operator in visualizing the specimen to be analyzed. Once the operator aligns the spectroscopic system and depresses the footswitch 224, the computer 202 controls the actions of the light sources 210, 212, the coupling optics 220, the transmission of light signals and electrical signals through the cable 106, the operation of the probe optics 230 and the scanner assembly 232, the retreival of observed spectra via the cable 106, the coupling of the observed spectra via the coupling optics 222 into the spectrometer and detector 218, the operation of the spectrometer and detector 218, and the subsequent signal procesing and analysis of the recorded spectra.

Figure 3:
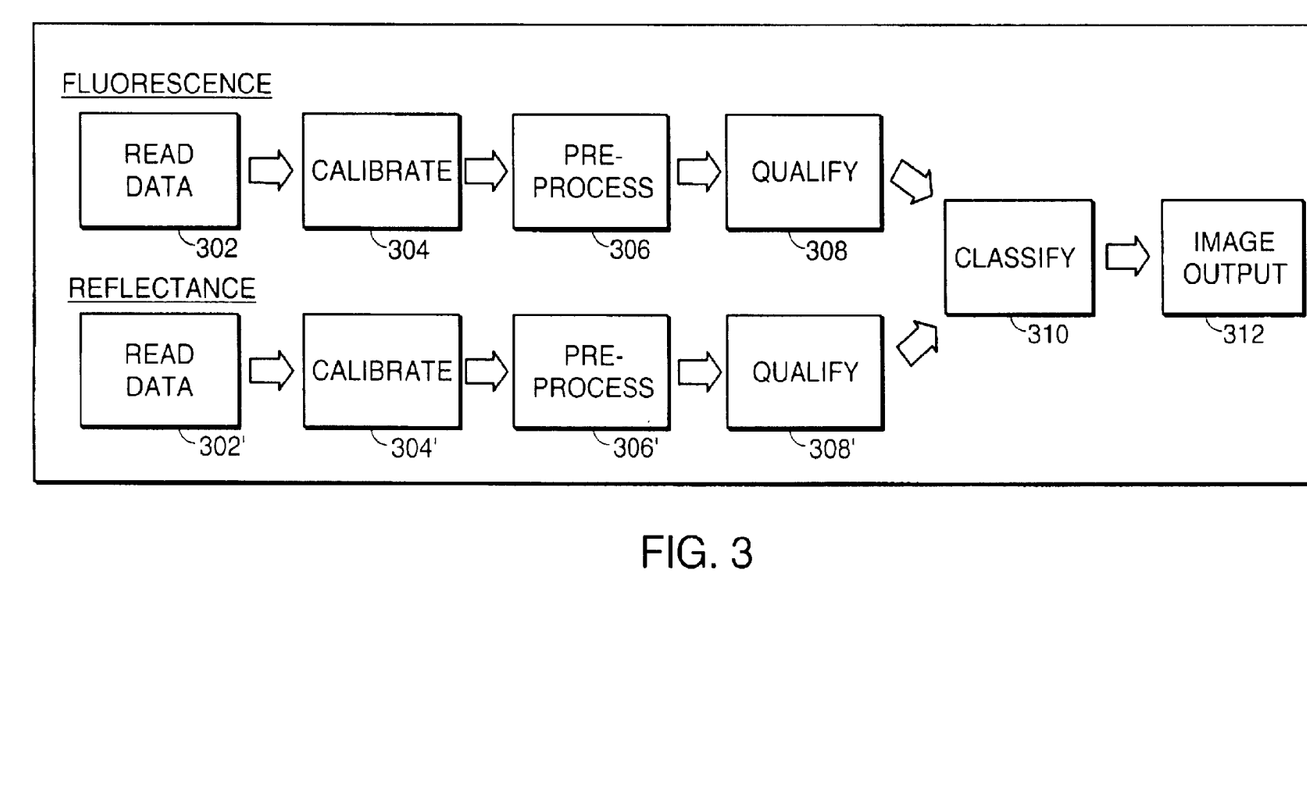
FIG. 3 is a schematic flow diagram of an illustrative spectral analysis process incorporating features of the invention.

FIG. 3 is a schematic flow diagram 300 of an illustrative spectral analysis process incorporating features of the invention. In FIG. 3, the flow of information for both the fluorescence spectra and the broadband reflectance spectra is explained in overview. FIG. 3 indicates that the computer 202 has processed one or more fluorescence spectra to the point where there is a suitable set of spectral results for analysis. With respect to fluorescence data, the illustrative analysis of FIG. 3 includes reading data 302, calibrating the data 304, pre-processing the data 306 and qualifying the data 308 as acceptable, valid data. With respect to the white light broadband reflectance spectra, the illustrative analysis of FIG. 3 includes reading the data 302', calibrating the data 304', pre-processing the data 306', and qualifying the data 308' as acceptable, valid data. The computer 202 combines the data obtained from the fluorescence spectra and the data obtained from the white light broadband reflectance spectra to classify the specimen in a classification step 310. As necessary, the spectroscopic system 100 generates an image from the two types of spectral data, and provides the image as output 312 in a form desired by the colposcopist/user, in either or both of a real-time video image or a recorded image in printed and/or electronic form.

Figure 4:
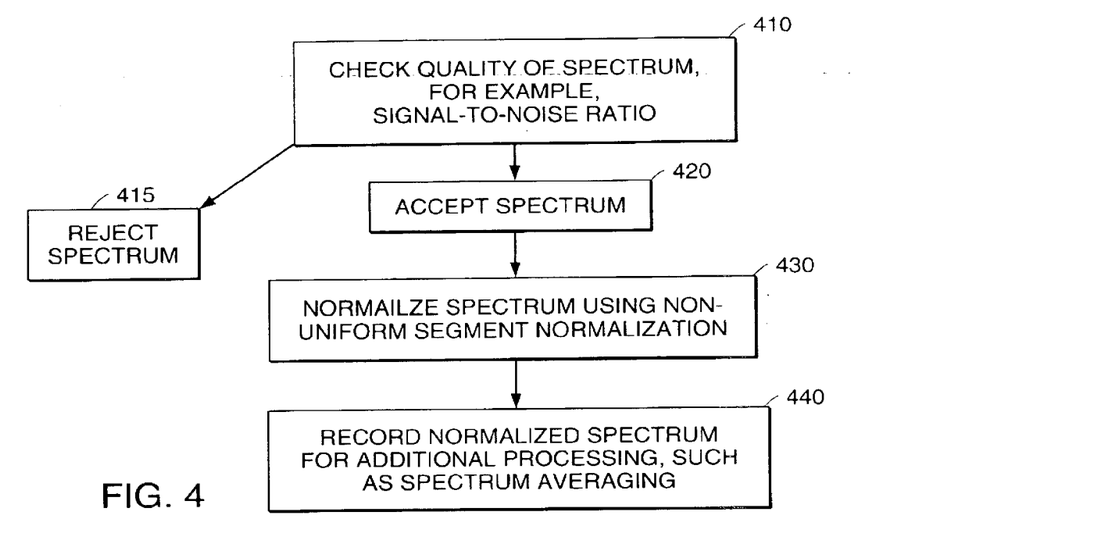
FIG. 4 is a more detailed schematic flow diagram depicting an exemplary calibration step of the type depicted in FIG. 3 and incorporating a non-uniform segment normalization method according to an illustrative embodiment of the invention.

FIG. 4 is a more detailed schematic flow diagram 400 depicting an exemplary calibration step 304, 304' of the type depicted in FIG. 3 and incorporating a non-uniform segment normalization method 430 according to an illustrative embodiment of the invention. In step 410, the illustrative spectroscopic system 100 performs a check of the quality of the spectrum, for example, by examining the signal-to-noise ratio of the spectrum to insure that the spectrum is of acceptable quality. In step 415, in response to the result of the check of step 410 showing an unacceptable spectral quality, the process 400 rejects the spectrum. As indicated in step 420, in response to the check of step 410 showing a sufficient spectral quality, the process 400 accepts the spectrum. As shown in step 430, the process 400 normalizes acceptable spectra using the non-uniform segment normalization method of the invention. As depicted in step 440, the process 400 records the normalized spectrum for further processing and analysis.

Figure 5:
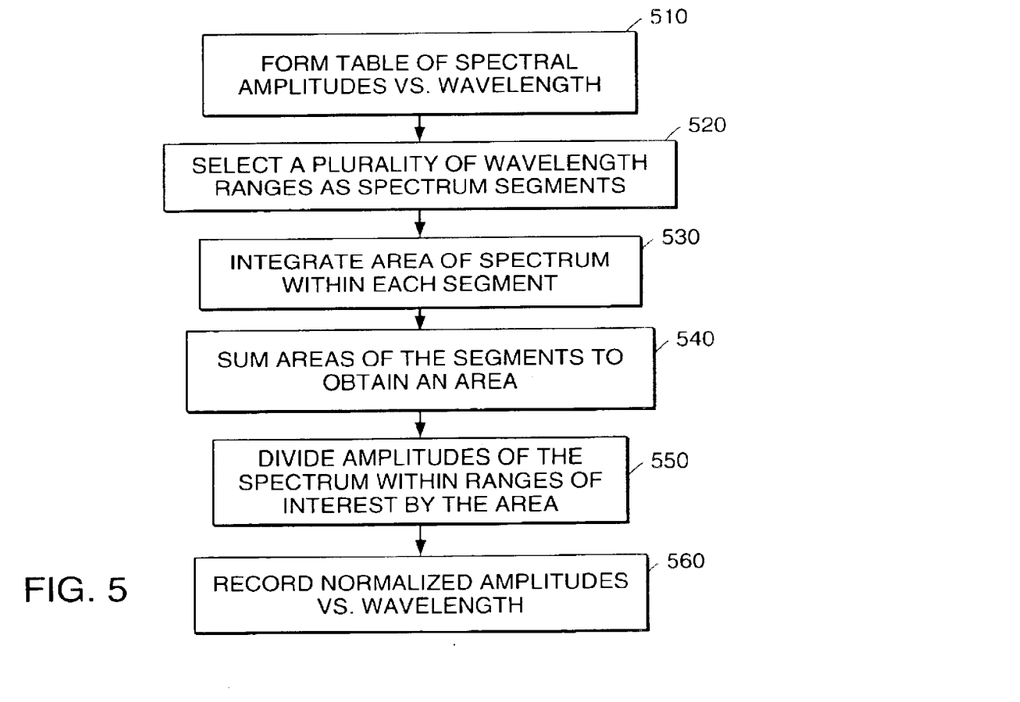
FIG. 5 is a detailed flow diagram that shows the steps of an exemplary non-uniform segment normalization method, according to an illustrative embodiment of the invention.

FIG. 5 is a more detailed flow diagram 500 showing an illustrative non-uniform segment normalization method according to the invention, in one embodiment, a detector detects the spectrum as amplitudes as a function of wavelength from the spectrometer. In a further embodiment, an analog-to-digital converter (A/D converter) converts the amplitude of the spectrum at each discrete wavelength to a digital value. The A/D converter provides output at a desired precision, such as 10-bits, 12-bits, 14-bits or even higher precision. As indicated at step 510, the digitized amplitudes so obtained are recorded in a computer memory or machine-readable record as a table of amplitudes recorded at selected discrete wavelengths. The computer 202 divides the spectrum into a plurality of portions, or segments of the spectrum, selected to span a range comprising one or more wavelengths. Each segment is bounded by an upper wavelength and a lower wavelength. As indicated at step 520, the computer 202 selects a subset of the plurality of segments for the normalization process. Alternatively, the user may select the subset of segments for normalization. The segments or ranges do not have to be uniform in width in wavelength space, nor do the segments need to be contiguous with each other or evenly separated in wavelength space. However, the segments may have uniform width, be contiguous and/or be evenly separated in wavelength space. The width of a wavelength range is defined as the absolute magnitude of a difference between an upper wavelength and a lower wavelength. Since the ranges and separations can be non-uniform in wavelength space, the method is referred to herein as the "non-uniform segment" normalization method.

The area of each segment is computed. As denoted in step 530, the area is calculated by summing a number n of strips. Each strip has an area determined by multiplying the amplitude at the particular wavelength corresponding to the strip by a range of wavelengths extending from that wavelength to the next longer discrete wavelength in the spectrum. This integration is expressed mathematically as $$A_i = \sum_{j=1}^{n} S(\lambda_j) |\lambda_{j+1} - \lambda_j|$$

where $A_j$ is the area of the $i^{th}$ segment, there are n amplitudes in the $i^{th}$ segment represented by a series of intensities or amplitudes at specific wavelengths, with n corresponding wavelength ranges, the amplitude S at wavelength $\lambda_i$ being denoted by $S(\lambda_i)$, and the difference $\lambda_{j+1}-\lambda_j$ representing the distance along the wavelength axis between successive amplitudes. This computation is also known as numerical integration. Skilled artisans will appreciate that any one of a number of methods may be used to determine the area of the segments of interest.

In step 540, a total area for all of the segments is determined by summing the values of the $A_i$. As shown in step 550, the computer 202 sums the areas $A_i$ to obtain the value NF, where NF is the normalization factor, and normalizes each of the amplitudes $S(\lambda_i)$ by dividing by the value NF, or by multiplying by the reciprocal of NF. The computer 202 obtains a normalized set of amplitudes. In step 560, the computer 202 records this normalized set of amplitudes as a new table of amplitude vs. wavelength. The normalized spectrum is denoted as:

$$S_A = \frac{1}{NF} S.$$

The computer 202 uses the normalized spectrum to determine a state of health or disease for the tissue specimen being examined.

Figure 6:
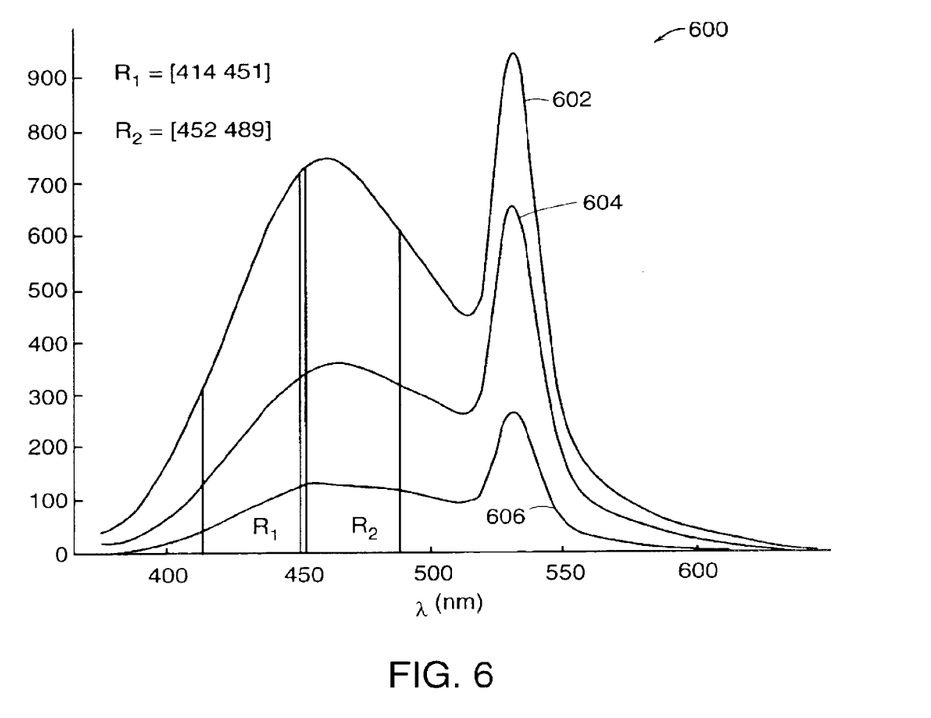
FIG. 6 is a graph depicting a selection of particular wavelength regions for applying a non-uniform segment normalization process according to an illustrative embodiment of the invention.

FIG. 6 is a graph 600 depicting a selection of particular wavelength regions for applying a non-uniform segment normalization process according to the invention. In one embodiment, the specimen is illuminated with ultraviolet radiation of a wavelength of 355 nm from a frequency-tripled Nd:YAG laser.

As depicted in FIG. 6, fluorescence spectra are recorded from various tissue specimens having different disease states, or different states of health. The spectrum 602 is typical of healthy cervical tissue comprising normal squamous cells. Cervical tissue can exhibit pre-cancerous lesions known as cervical intraepithelial neoplasia (CIN), a condition that has been divided into three grades. CIN I is the mildest form of the neoplasia, and most often regresses to normal tissue without intervention. CIN II and CIN III are more severe grades of the neoplasia, with CIN III being a potential signal for progression into carcinoma in-situ (CIS). Often the course of treatments for CIN II and CIN III are similar, including removal of the tissue through biopsy or Loop Electro-Excision Procedure (LEEP), so pathologists usually combine the diagnosis of CIN II and CIN III together as CIN II/III. The spectrum 604 in FIG. 6 is typical of CIN II/III. The spectrum 606 is typical of CIN I.

In FIG. 6, two regions are indicated by vertical lines that intersect the three spectra 602, 604, 606. These vertical lines define two regions, one labeled R1, extending from the wavelengths 414 nm to 451 nm inclusive, and another labeled R2, extending from 452 nm to 489 nm inclusive. In one embodiment of the non-uniform segment normalization method, these regions are selected. These spectral regions provide data that most readily distinguish the conditions of normal health and of CIN II/III. It is not helpful to use spectral information that lies outside these two regions. Such use risks introducing artifacts that may render it more difficult to discriminiate between the conditions of normal health and CIN II/III. For example, in the spectra of FIG. 6, each spectrum 602, 604, 606 exhibits a maximum value at a wavelength of approximately 532 nm, which is outside the range of interest. Peak normalization using the 532 nm line runs the risk that an error in a non-meaningful datum can skew the data in the region of interest. Alternatively, area normalization using the area of each spectrum over the entire spectral range of approximately 370 nm to approximately 600 nm also runs the risk of normalizing the useful data using an area heavily influenced by non-meaningful data.

According to an illustrative embodiment of the invention, the computer 202 computes a test parameter, for example, the average value of the normalized amplitude within each region that has been selected. In the embodiment described in FIG. 6, the computer 202 can, for example, compute the average normalized amplitude for region R1 and the average normalized amplitude for region R2.

The computer 202 uses the spectra normalized using the non-uniform segment normalization to determine a disease state or a state of health of the specimen from which they were recorded (i.e., the test specimen). In one embodiment, the computer 202 performs the analysis by comparing the spectra obtained from the test specimen to spectra obtained from known healthy and diseased specimens (i.e., known spectra). The computer 202 determines which known spectrum the spectrum obtained from the test specimen most closely resembles. In the embodiment described in FIG. 6, the computer 202 can compare the test parameters computed by finding the average normalized amplitude within region R1 and within region R2 to the same parameters computed for specimens of known health status.

Equivalents

While the invention has been particularly shown and described with reference to specific preferred embodiments, it should be understood by skilled artisans that various changes in form and detail may be made therein without departing from the spirit and scope of the invention as defined by the appended claims.

What is claimed is:

1. A method of performing spectral analysis, the method comprising:
   obtaining an optical spectrum, and
   normalizing said optical spectrum by application of non-uniform segment normalization, said normalizing step comprising:
     selecting one or more segments from said optical spectrum, each of said segments being bounded by an upper wavelength and a lower wavelength and containing one or more wavelengths, each of said wavelengths having an associated amplitude,
     determining an area under a curve associated with each particular segment, wherein each said curve is bounded along a first axis by said upper wavelength and said lower wavelength of said particular segment, and along a second axis by amplitudes associated with each of said wavelengths included in said particular segment,
     summing said areas for each of said segments to determine a normalization factor, and
     dividing at least one said associated amplitude for one of said wavelengths included in said segments by said normalization factor.

2. The method of claim 1, wherein a first segment differs in size of wavelength range from that of a second segment, wherein said size of wavelength range is defined as the absolute magnitude of a difference between said upper wavelength and said lower wavelength.

3. The method of claim 1, wherein a first segment is equal in wavelength range to a second segment, wherein said size of wavelength range is defined as the absolute magnitude of a difference between said upper wavelength and said lower wavelength.

4. The method of claim 1, wherein said one or more segments comprises at least first and second non-contiguous segments.

5. The method of claim 1, wherein said one or more segments comprises at least first, second and third segments, and there exists a first span between an upper wavelength of said first segment and a lower wavelength of said second segment, and a second span between an upper wavelength of said second segment and a lower wavelength of said third segment.

6. The method of claim 5, wherein said first and said second spans differ in magnitude.

7. The method of claim 5, wherein said first and said second spans are substantially equal in magnitude.

8. The method of claim 1, further comprising obtaining said spectrum from a specimen of human cervical tissue.

9. The method of claim 1, further comprising determining a disease status of said test specimen by analyzing said optical spectrum subsequent to said normalizing.

10. A system for performing spectral analysis comprising:
    a spectrographic device adapted to obtain an optical spectrum from a test specimen,
    a processor adapted to normalize said optical spectrum by application of non-uniform segment normalization, and
    machine-readable instructions executing on said processor and adapted to:
      select one or more segments from said optical spectrum, each of said segments being bounded by an upper wavelength and a lower wavelength, and containing one or more wavelengths, each of said wavelengths having an associated amplitude,
      determine an area under a curve associated with each particular one of said segments, wherein each said curve is bounded along a first axis by said upper wavelength and said lower wavelength of said particular segment, and along a second axis by said amplitudes associated with each of said wavelengths included in said particular segment,
      sum said areas for each of said segments to determine a normalization factor, and
      divide at least one said associated amplitude for one of said wavelengths included in said segments by said normalization factor.

11. The system of claim 10, wherein said machine readable instructions are further adapted to one of select and enable a user to select a first segment different in size of wavelength range from that of a second segment, wherein said size of wavelength range is defined as the absolute magnitude of a difference between said upper wavelength and said lower wavelength.

12. The system of claim 10, wherein said machine readable instructions are further adapted to one of select and enable a user to select a first segment to be substantially equal in size of wavelength range to that of a second segment, wherein said size of wavelength range is defined as the absolute magnitude of a difference between said upper wavelength and said lower wavelength.

13. The system of claim 10, wherein said machine readable instructions are further adapted to one of select and enable a user to select said one or more segments to include at least first and second non-contiguous segments.

14. The system of claim 10, wherein said machine readable instructions are further adapted to one of select and enable a user to select said one or more segments to include at least first, second and third segments, and there exists a first wavelength span between an upper wavelength of said first segment and a lower wavelength of said second segment, and a second wavelength span between an upper wavelength of said second segment and a lower wavelength of said third segment.

15. The system of claim 14, wherein said first and said second spans differ in magnitude.

16. The system of claim 14, wherein said first and said second spans are substantially equal in magnitude.

17. The system of claim 10, wherein said spectrographic device is further adapted to obtain said optical spectrum from a specimen of human cervical tissue.

18. The system of claim 10, wherein said machine readable instructions are further adapted to extract a test parameter from said optical spectrum.

19. The system of claim 10, wherein said machine readable instructions are further adapted to determine a disease status of said test specimen by analyzing said optical spectrum, subsequent to said normalizing.

* * * * *